(12) United States Patent
Cheng et al.

(10) Patent No.: US 7,837,693 B2
(45) Date of Patent: Nov. 23, 2010

(54) RETRIEVAL DEVICE WITH LASER CUT BASKET

(75) Inventors: Eric Cheng, Bloomington, IN (US); James A. Teague, Spencer, IN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1182 days.

(21) Appl. No.: 11/449,793

(22) Filed: Jun. 9, 2006

(65) Prior Publication Data

US 2007/0288037 A1 Dec. 13, 2007

(51) Int. Cl.
*A61M 29/00* (2006.01)
(52) U.S. Cl. ..................................... 606/127
(58) Field of Classification Search ................ 606/127, 606/200, 114, 128
See application file for complete search history.

(56) References Cited

U.S. PATENT DOCUMENTS

| 2001/0001315 A1* | 5/2001 | Bates et al. ................. 606/114 |
| 2005/0027245 A1* | 2/2005 | Sachdeva et al. ............ 606/200 |
| 2005/0119668 A1* | 6/2005 | Teague et al. ................ 606/127 |

* cited by examiner

*Primary Examiner*—Todd E Manahan
*Assistant Examiner*—Naquan Ishman
(74) *Attorney, Agent, or Firm*—Finnegan Henderson Farabow Garrett & Dunner, L.L.P.

(57) ABSTRACT

A medical device includes a sheath defining a lumen, and an elongate member movably disposed within the lumen. The elongate member includes a basket having a plurality of legs, at least one leg of the plurality of legs is disposed between adjacent first and second slots defined by the elongate member. A first distal relief feature at a distal end of the first slot is longitudinally offset from a second distal relief feature at a distal end of the second slot.

38 Claims, 2 Drawing Sheets

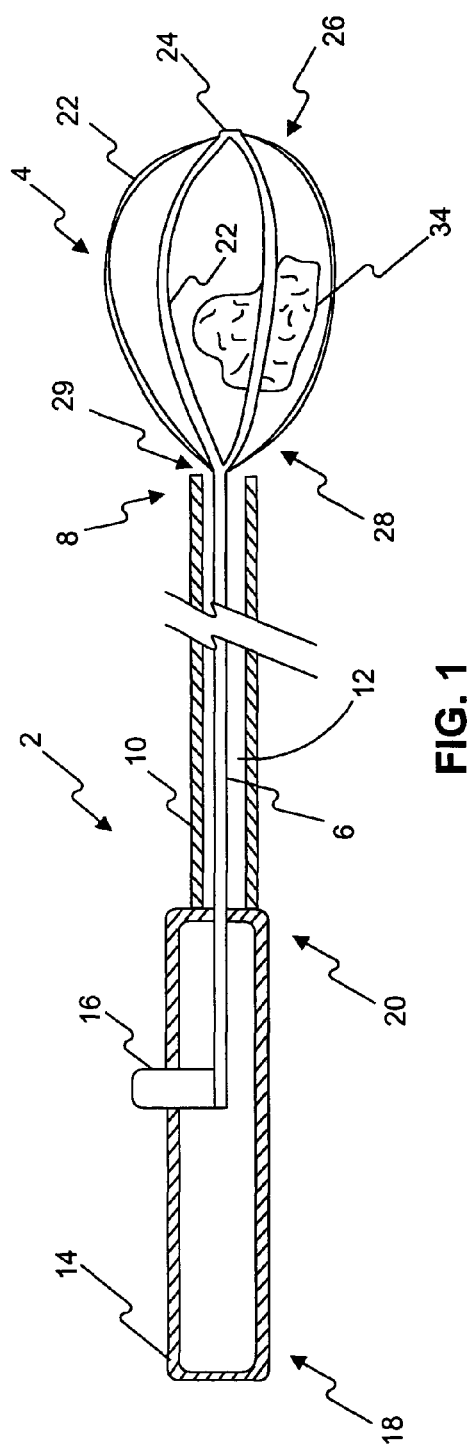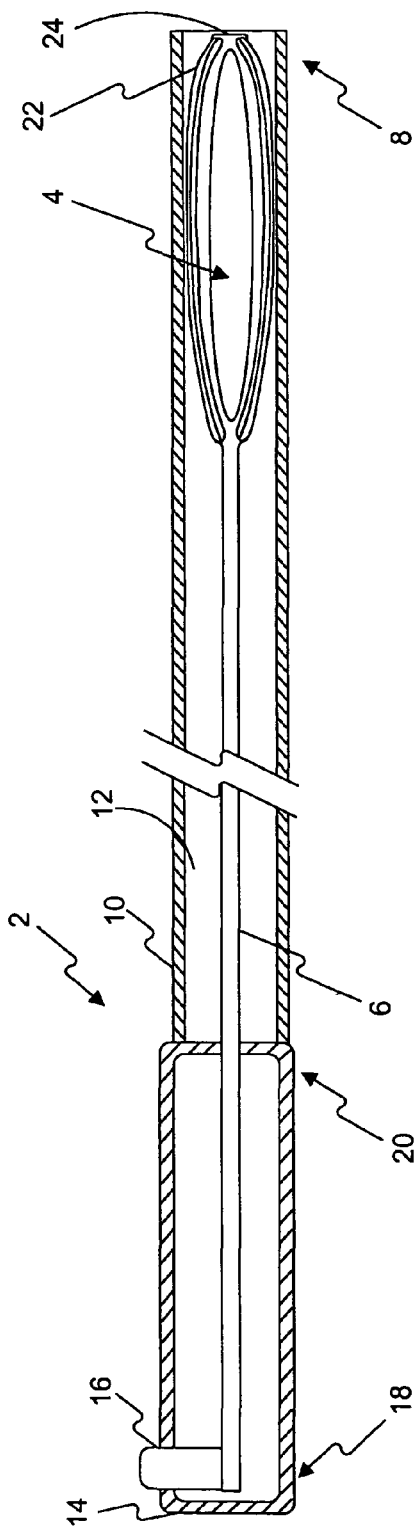

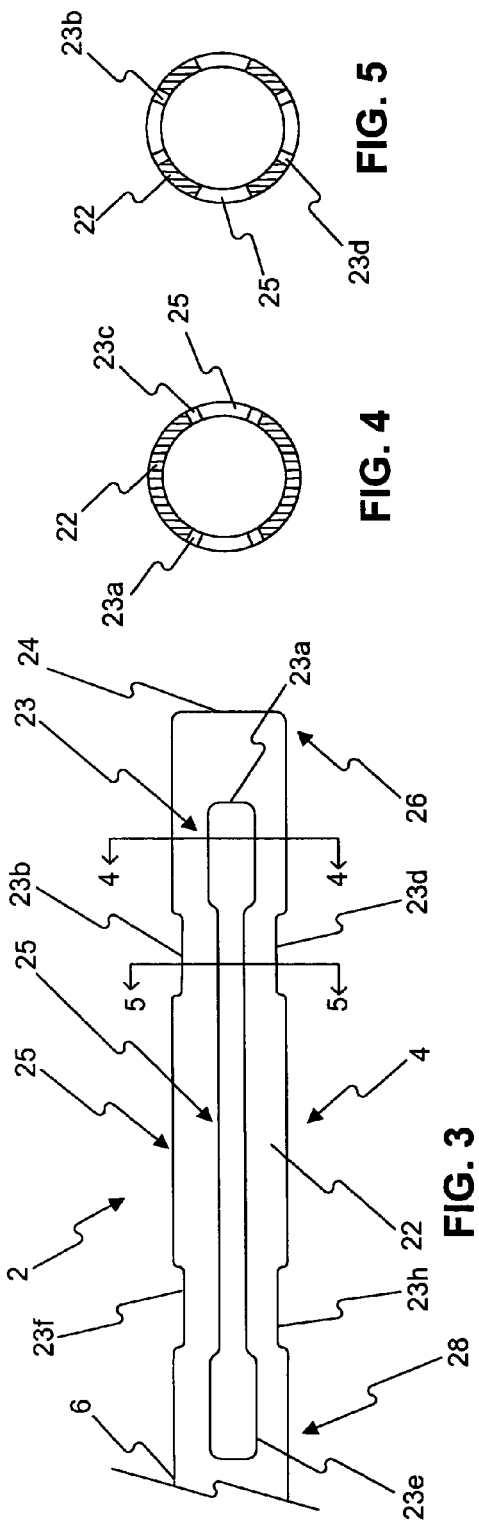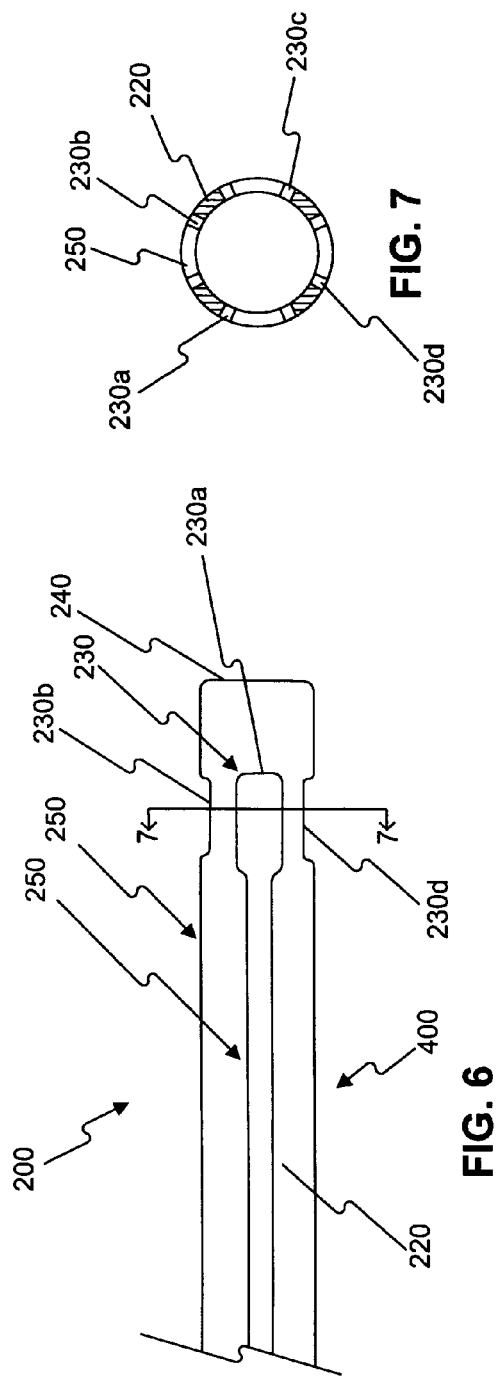

RETRIEVAL DEVICE WITH LASER CUT BASKET

FIELD OF THE INVENTION

This disclosure relates generally to a medical device and, more particularly, to retrieval devices having laser cut baskets and methods of manufacturing and using the same.

BACKGROUND OF THE INVENTION

Extractors have been used for the removal of stones, calculi, and other foreign matter from within the body. One type of extractor has a sheath and includes a basket at its distal end. The basket may be collapsed within the sheath to achieve a reduced diameter profile. The basket may also be opened when it extends beyond the sheath. Once opened, a targeted stone may be captured within the basket. The baskets of such extractors may include wires that are joined via soldering or welding to form a tip at a distal end of the basket. The baskets of other extractors may have wires that are twisted or knotted together at the distal end. Manufacturing such devices, however, can be costly and time consuming. In addition, the tips of these devices may hinder access to the targeted stone and may increase the possibility of tissue damage within the body.

The present disclosure provides retrieval devices and methods of manufacturing and using the same that avoid some or all of the aforementioned shortcomings of existing devices.

SUMMARY OF THE INVENTION

In an exemplary embodiment of the present disclosure, a medical device includes a sheath defining a lumen, and an elongate member movably disposed within the lumen. The elongate member includes a basket having a plurality of legs, at least one leg of the plurality of legs is disposed between adjacent first and second slots defined by the elongate member. A first distal relief feature at a distal end of the first slot is longitudinally offset from a second distal relief feature at a distal end of the second slot.

In accordance with certain embodiments of the present disclosure, the device may include one or more of the following features. For example, the elongate member and the basket are formed from a single piece of a material, the first and second slots extend substantially longitudinally along the elongate member, and the first and second slots are formed by removing portions of the elongate member. In addition, at least one of the relief features is an extension of a corresponding slot, at least one of the relief features is a widened end of a corresponding slot, and at least one of the relief features is an opening in a wall of the elongate member. The at least one relief feature has a width greater than a width of a corresponding slot.

Moreover, in certain embodiments, a first proximal relief feature is disposed at a proximal end of the first slot and a second proximal relief feature is disposed at a proximal end of the second slot, the first proximal relief feature is longitudinally offset from the second proximal relief feature. In such an exemplary device, the first proximal relief feature has a first width dimension, the first distal relief feature has a second width dimension, and the first slot has a third width dimension, the first and second width dimensions are larger than the third width dimension. In addition, the first distal relief feature is substantially completely proximal the second distal relief feature and the first proximal relief feature is substantially completely distal the second proximal relief feature. Alternatively, the first distal relief feature is substantially completely proximal the second distal relief feature and the first proximal relief feature is substantially completely proximal the second proximal relief feature.

Such exemplary devices also may include a third slot defined by the elongate member and disposed adjacent to at least one of the first slot and the second slot. A third distal relief feature at a distal end of the third slot is longitudinally offset from an adjacent distal relief feature. In such a device, the third distal relief feature is substantially completely proximal the second distal relief feature, and a third proximal relief feature at a proximal end of the third slot is substantially completely proximal the second proximal relief feature.

In addition, in certain embodiments, such baskets include at least four legs and the basket includes a predetermined shape in an expanded position. The elongate member is substantially hollow.

In another exemplary embodiment of the present disclosure, a medical retrieval device basket includes a plurality of legs, each of the legs is defined by at least two slots of an elongate member. A first distal relief feature is disposed at a distal end of a first slot and a second distal relief feature is disposed at a distal end of a second slot. The first slot is adjacent the second slot, and the first distal relief feature is longitudinally offset from the second distal relief feature.

In accordance with certain embodiments of the present disclosure, the device may include one or more of the following features. For example, the at least two slots extend substantially longitudinally along the elongate member and the at least two slots are formed by removing portions of the elongate member. At least one of the relief features is an extension of a corresponding slot and at least one of the relief features is a widened end of a corresponding slot. At least one of the relief features is an opening in a wall of the elongate member and the at least one relief feature has a width greater than a width of a corresponding slot.

Moreover, in certain embodiments, a first proximal relief feature at a proximal end of the first slot has a first width dimension, the first distal relief feature has a second width dimension, and the first slot has a third width dimension. The first and second width dimensions are larger than the third width dimension. The first distal relief feature is substantially completely proximal the second distal relief feature, and the first proximal relief feature is substantially completely distal a second proximal relief feature at a proximal end of the second slot. Alternatively, the first distal relief feature is substantially completely proximal the second distal relief feature, and the first proximal relief feature is substantially completely proximal a second proximal relief feature at a proximal end of the second slot.

Such exemplary devices also may include a third slot defined by the elongate member and disposed adjacent to at least one of the first slot and the second slot. A third distal relief feature at a distal end of the third slot is longitudinally offset from an adjacent distal relief feature. In such a device, the third distal relief feature is substantially completely proximal the second distal relief feature, and a third proximal relief feature at a proximal end of the third slot is substantially completely proximal a second proximal relief feature at a proximal end of the second slot.

In addition, in certain embodiments, such baskets include at least four legs, the basket includes a predetermined shape in an expanded position, and the elongate member is substantially hollow.

In a further exemplary embodiment of the present disclosure, a method of manufacturing a medical device includes removing longitudinal portions of a piece of material to form a basket having a plurality of legs defined by slots. The method further includes removing second portions of the piece of material to form a first distal relief feature at a distal end of a first slot and a second distal relief feature at a distal end of a second slot. The first distal relief feature is longitudinally offset from the second distal relief feature, and the first slot is adjacent to the second slot.

In accordance with certain embodiments of the present disclosure, the method may include one or more of the following features. For example, removing longitudinal portions of the piece of material includes one of laser cutting, chemical etching, die cutting, and mechanically slicing. Removing second portions of the piece of material includes one of laser cutting, chemical etching, die cutting, and mechanically slicing. Removing second portions of the piece of material further includes forming a first proximal relief feature at a proximal end of the first slot and a second proximal relief feature at a proximal end of the second slot. The first proximal relief feature is longitudinally offset from the second proximal relief feature. The first proximal relief feature has a first width dimension, the first distal relief feature has a second width dimension, and the first slot has a third width dimension, the first and second width dimensions are larger than the third width dimension. The first distal relief feature is substantially completely proximal the second distal relief feature, and the first proximal relief feature is substantially completely distal the second proximal relief feature. Alternatively, the first distal relief feature is substantially completely proximal the second distal relief feature, and the first proximal relief feature is substantially completely proximal the second proximal relief feature.

In an additional embodiment, the method further includes forming a third slot defined by the elongate member and disposed adjacent to at least one of the first slot and the second slot. A third distal relief feature at a distal end of the third slot is longitudinally offset from an adjacent distal relief feature. The third distal relief feature is substantially completely proximal the second distal relief feature, and a third proximal relief feature at a proximal end of the third slot is substantially completely proximal the second proximal relief feature. The basket comprises at least four legs.

In still another exemplary embodiment of the present disclosure, a method of removing matter from the body of a patient includes providing a medical device including a sheath defining a lumen, and an elongate member movably disposed within the lumen. The elongate member includes a basket having a plurality of legs, at least one leg of the plurality of legs is disposed between adjacent first and second slots defined by the elongate member. A first distal relief feature at a distal end of the first slot is longitudinally offset from a second distal relief feature at a distal end of the second slot. The method also includes advancing the medical device to a treatment site within the body of the patient and capturing the matter within the basket of the device. The method further includes removing the medical device from the body of the patient.

In accordance with certain embodiments of the present disclosure, the method may include one or more of the following features. For example, the method also includes immobilizing the matter with the plurality of legs of the basket, reducing the size of the matter, and sweeping at least a portion of the matter from the treatment site with the plurality of legs of the basket. The matter is one of a kidney stone, a struvite, a uric acid stone, a cystine stone, and a solid deposit.

In addition, in methods according to certain embodiments, a first proximal relief feature is disposed at a proximal end of the first slot, and a second proximal relief feature is disposed at a proximal end of the second slot. The first proximal relief feature is longitudinally offset from the second proximal relief feature. The first proximal relief feature has a first width dimension, the first distal relief feature has a second width dimension, and the first slot has a third width dimension. The first and second width dimensions are larger than the third width dimension. The first distal relief feature is substantially completely proximal the second distal relief feature, and the first proximal relief feature is substantially completely distal the second proximal relief feature. Alternatively, the first distal relief feature is substantially completely proximal the second distal relief feature, and the first proximal relief feature is substantially completely proximal the second proximal relief feature.

In another exemplary embodiment of the method, a third slot is defined by the elongate member and disposed adjacent to at least one of the first slot and the second slot. A third distal relief feature at a distal end of the third slot is longitudinally offset from an adjacent distal relief feature. The third distal relief feature is substantially completely proximal the second distal relief feature, and a third proximal relief feature at a proximal end of the third slot is substantially completely proximal the second proximal relief feature.

It is to be understood that both the foregoing general description and the following detailed description are exemplary and explanatory only, and are not restrictive of the invention as claimed.

BRIEF DESCRIPTION OF THE DRAWINGS

FIG. 1 is a partial cross-sectional view of a retrieval device according to an exemplary embodiment of the present disclosure.

FIG. 2 illustrates an alternate configuration of the device of FIG. 1.

FIG. 3 is a side view of a portion of the device of FIG. 1.

FIG. 4 is a cross-sectional view of the device of FIG. 3.

FIG. 5 is another cross-sectional view of the device of FIG. 3.

FIG. 6 is a side view of a portion of another retrieval device.

FIG. 7 is a cross-sectional view of the device of FIG. 6.

DETAILED DESCRIPTION

Exemplary embodiments of the present disclosure are illustrated in the accompanying drawings. Wherever possible, the same reference numbers will be used throughout the drawings to refer to the same or like parts.

FIG. 1 illustrates a retrieval device 2 according to an exemplary embodiment of the present disclosure. The device 2 includes a basket 4 connected to an elongate member 6. The device 2 further includes a sheath 10 defining a lumen 12, and the elongate member 6 is disposed within the lumen 12. Relative movement between the elongate member 6 and the sheath 10 assists the basket 4 in forming an expanded position (shown in FIG. 1) where the basket 4 is disposed beyond a distal end 8 of the sheath 10, and a retracted position (shown in FIG. 2) where the basket 4 is disposed within the lumen 12 of the sheath 10.

The basket 4 may include a plurality of legs 22. The legs 22 and, thus, a proximal end 28 of the basket 4 may be connected to a distal end 29 of the elongate member 6 in any conventional way. As will be described below, in an exemplary embodiment, the legs 22 may be formed of the same piece or pieces of material as the elongate member 6. Although FIGS. 1 and 2 show a basket 4 having four legs 22, other exemplary embodiments of the basket 4 may include more or fewer than four legs 22 to facilitate the retrieval of a stone 34, calculi, or other foreign matter. The basket 4 may further include an atraumatic tip 24 at a distal end 26 of the basket 4. The atraumatic tip 24 may have any atraumatic configuration known in the art. For example, the atraumatic tip 24 may be a filled, crimped, and/or capped distal end 26 of the elongate member 6.

The device 2 may also include a handle 14 configured to assist in transitioning the basket 4 between the expanded position and the retracted position. The handle 14 may include, for example, a thumb slide 16 or other conventional mechanisms configured to assist in manipulating the position of the basket 4. In an exemplary embodiment, moving the thumb slide 16 toward a distal end 20 of the handle 14 may move the elongate member 6 and the basket 4 in a distal direction relative to the handle 14 and, thus, assist in transitioning the basket 4 to the expanded position shown in FIG. 1. In such an embodiment, moving the thumb slide 16 toward a proximal end 18 of the handle 14 may move the elongate member 6 and the basket 4 in a proximal direction relative to the handle 14 and, thus, assist in transitioning the basket 4 to the retracted position shown in FIG. 2. In this exemplary embodiment, the sheath 10 may remain stationary with respect to the handle 14. In an additional exemplary embodiment, the elongate member 6 and the basket 4 may remain stationary with respect to the handle 14, and the thumb slide 16 may be configured to move the sheath 10 relative to the basket 4.

The elongate member 6 may be formed from, for example, a wire, rod, tube, hypotube, cannula, stent, or other piece of biocompatible material or combination of biocompatible materials known in the art. Such materials may include, but are not limited to, polyamide, PEBAX, stainless steel (such as 300 and 400 series), cobalt, chromium, nickel, titanium, nitinol, thermoforming plastic, polytetrafluoroethylene ("PTFE"), and expanded polytetrafluoroethylene ("ePTFE"). The elongate member 6 may also be a metal coated with a polymer and may have one or more layers of material. The elongate member 6 may be solid or hollow, and may be substantially cylindrical. Alternatively, the elongate member 6 may be formed from a flat sheet of material. If formed from a flat sheet, the elongate member 6 may be formed into a substantially cylindrical shape.

The overall length and diameter of the elongate member 6 may vary depending on the application. For example, a relatively long elongate member 6 may be advantageous for retrieving stones or other calculi deep within the body of the patient. In addition, an elongate member 6 having a relatively small diameter may be advantageous for retrieving stones from restricted passageways within the human urinary tract. The elongate member 6 may be relatively flexible to facilitate the retrieval of stones located in complex, tortuous body structures.

The sheath 10 may be formed from any of the materials discussed above with respect to the elongate member 6. Although FIGS. 1 and 2 illustrate a sheath 10 having a single lumen 12, in additional exemplary embodiments of the present disclosure, the sheath 10 may define more than one lumen 12. The sheath 10 may be dimensioned to fully enclose the elongate member 6 and the basket 4 when the basket 4 is in the retracted position shown in FIG. 2.

The legs 22 of the basket 4 may be formed by, for example, laser cutting, chemical etching, die cutting, or mechanically slicing a single piece of material. The single piece of material may be the same piece of material as the elongate member 6. The width of the cuts may define the width and mechanical behavior of each of the basket legs 22, and the desired width may vary depending on the particular application. For example, it may be advantageous to have relatively narrow basket legs 22 when retrieving a relatively large stone 34 from a body structure. The length of the cuts may define the length and mechanical behavior of the basket legs 22, and the desired length may vary depending on the particular application. Each leg 22 may have the same length and width, or the length and width of each leg 22 may vary depending on the particular application. In addition, the spacing between the legs 22 may vary or be consistent.

The cuts made through the wall of the elongate member 6 form a plurality of slots 25. As illustrated in FIG. 3, the slots 25 extend substantially longitudinally from the distal end 26 of the basket 4 to the proximal end 28, and the number of slots 25 may correspond to the number of legs 22 desired. The legs 22 may be of any length, width, or shape depending on the slots 25 described above. For example, as shown in FIG. 3, the slots 25 may be substantially straight resulting in substantially straight legs 22. The slots 25 are further illustrated in FIGS. 4 and 5. Alternatively, the slots 25 may be, for example, wave-shaped, v-shaped, saw-shaped, or any other shape to achieve desirable characteristics of legs 22. Such slots 25 may result in legs 22 having improved stone retrieval characteristics.

The legs 22 may be, for example, cold worked or heat processed to form a shape in memory. The shape of the legs 22 may be fully formed once the sheath 10 is retracted and the basket 4 is allowed to fully expand. Alternatively, the shape may be partially formed when the sheath 10 is partially retracted. The resulting basket 4 may be any shape useful in capturing and/or retrieving a stone 34 (FIG. 1) or other calculi or foreign matter, and may be sized so as to be capable of capturing a stone 34 in the range of approximately 4 mm to approximately 10 mm along its largest dimension. Such baskets 4 may be, for example, substantially spherical or substantially lemon-shaped.

Cuts made through the wall of the elongate member 6 may also form a plurality of relief features 23 therein. In an exemplary embodiment, a relief feature 23 may be disposed only at a distal end of a slot 25. In an additional exemplary embodiment, a relief feature 23 may be disposed at each of the proximal and distal ends of a slot 25. Each slot 25 may include relief features 23. The relief features 23 may be widened ends of the slots 25, and may have any shape, size, and/or other configuration. Such relief features 23 may be, for example, substantially rectangular, substantially circular, and/or substantially elliptical. The relief features 23 may provide stress fracture and/or split propagation relief for the slots 25. For example, the relief features 23 may assist a corresponding slot 25 in resisting tearing proximally and/or distally as a result of repeated opening and closing of the basket 4. Each relief feature 23 may have a width dimension that is larger than a width dimension of a corresponding slot 25. In an exemplary embodiment, each of the relief features 23 may have substantially the same width dimension. Alternatively, in an additional exemplary embodiment, the width dimension of the relief features 23 may not be equal.

As shown in FIGS. 6 and 7, a retrieval device 200 may include a basket 400 having a plurality of legs 220 defined by a plurality of slots 250. Each slot 250 may include at least one relief feature 230. In such an embodiment, a first, second, third, and fourth relief feature 230*a*, 230*b*, 230*c*, 230*d* may be substantially aligned, i.e. at the same position longitudinally along the basket 400. Aligning the relief features 230 as shown in FIGS. 6 and 7, to form a basket 400 having legs 220 of a desired cross-sectional area, may require an increased diameter elongate member 6 to allow adequate room for the adjacent relief features 230. The configuration of FIGS. 6 and 7 may also result in the formation of thin wall regions between adjacent legs 220 (such as, for example, along line 7-7). Such thin wall regions may reduce the integrity of the basket 400 and/or the atraumatic tip 240. Exemplary thin wall regions are illustrated by the cross-section of legs 220 shown in FIG. 7.

As shown in FIGS. 3-5, in an exemplary embodiment of the invention, each relief feature 23 may be offset from an adjacent relief feature 23. For example, a basket 4 may have four legs 22, each leg 22 including a proximal and a distal relief feature 23. In such an exemplary basket 4, a first distal relief feature 23a may be disposed substantially completely distal a second distal relief feature 23b, the second distal relief feature 23b may be disposed substantially completely proximal a third distal relief feature 23c, and the third distal relief feature 23c may be disposed substantially completely distal a fourth distal relief feature 23d. In addition, in such an exemplary basket 4, a first proximal relief feature 23e may be disposed substantially completely proximal a second proximal relief feature 23f, the second proximal relief feature 23f may be disposed substantially completely distal a third proximal relief feature (not shown) corresponding to relief feature 23c, and the third proximal relief feature may be disposed substantially completely proximal a fourth proximal relief feature 23h. In such an embodiment, the basket 4 may include a first pair of slots 25 having a length that is different than a second pair of slots 25. For example, in such an embodiment, a first pair of slots 25 may have a length that is greater than a second pair of slots 25.

Alternatively, in another exemplary basket 4, the second and fourth proximal relief features 23f, 23h, may be disposed substantially completely proximal the first and third proximal relief features 23e, (not shown), respectively. In such an exemplary embodiment, each of the slots 25 may have substantially the same length. In still another exemplary basket 4, the first distal relief feature 23a may be substantially completely distal the second distal relief feature 23b, the second distal relief feature 23b may be substantially completely distal the third distal relief feature 23c, and the third distal relief feature 23c may be substantially completely distal the fourth distal relief feature 23d. In such an exemplary embodiment, the first proximal relief feature 23e may be substantially completely distal the second proximal relief feature 23f, the second proximal relief feature 23f may be substantially completely distal the third proximal relief feature, and the third proximal relief feature (not shown) may be substantially completely distal the fourth proximal relief feature 23h. In such an exemplary embodiment, each of the slots 25 may have substantially the same length. Other arrangements of staggered, offset relief features 23, such that adjacent relief features 23 are at different positions longitudinally along the basket 4, are within the scope of the invention.

Aligning the relief features 23 in such a manner may maximize the useable surface area of an elongate member 6. In other words, such offset alignments may maximize the possible number of legs 22 in an elongate member 6 of a given diameter. Such configurations may also maximize the cross-sectional area of each basket leg 22 formed of the elongate member 6. In particular, such configurations may maximize the cross-sectional area of the legs 22 at the locations of the relief features 23 (such as, along the lines 4-4 and 5-5 shown in FIG. 3) and may reduce the number of thin wall regions between adjacent legs 22. Thus, offsetting the relief features 23 as described above may minimize slot propagation and/or tearing, and may improve the integrity of the basket 4 and/or the atraumatic tip 24.

The basket 4 described above may also include webbing, netting, or any other retrieval material (not shown) disposed between at least a portion of at least two of the basket legs 22. The retrieval material may be, for example, polyvinylethylene ("PVE"), polyvinyl alcohol ("PVA"), ePTFE, PTFE, foam, rubber, plastic, polyurethane, or any other polymer or composite known in the art. The retrieval material may form a partial barrier between the legs 22 of the basket 4, and may extend partially or completely along the length of the legs 22 between which it is disposed. The retrieval material may allow, for example, fluid or other material to pass through while prohibiting, for example, stones from escaping the basket 4. The retrieval material may be attached to the legs 22 through welding, grafting, tying, or any other attachment method known in the art. The legs 22 of the basket 4 may also be coated with a sheet of protection material (not shown) to protect the legs 22 during processes such as, for example, laser lithotripsy. The configuration, material, and other characteristics of the basket 4 described herein permit the basket 4 to assume a contracted, collapsed state within the sheath 10 for delivery to a treatment site, and an expanded state for use at the treatment site.

At least some aspects of the present disclosure may be used, for example, to retrieve a stone 34, calculus, or other material from any location within the body, such as, for example, in the urinary tract of the patient. The device 2 may be inserted through the urethra of the patient or, alternatively, the device 2 may be inserted percutaneously to a treatment site. The treatment site within the body may correspond to the location of a targeted stone 34.

The stone 34 targeted for retrieval may be a kidney stone, a struvite, a uric acid stone, a cystine stone, or other solid deposit commonly removed from a body structure or passageway within the body. Such stones 34 may contain various combinations of chemicals, including, but not limited to, calcium, oxalate, and phosphate. The stone 34 may be of any size and could have a length or diameter of approximately 1 mm to 12 mm. These lengths and diameters are merely exemplary, and aspects of the present disclosure may assist in the retrieval of stones larger or smaller than those discussed herein. Stones 34 may be of any shape and could be, for example, flat, round, smooth, or jagged. The device 2 may retrieve stones 34 that are both impacted and free floating.

The device 2 may be advanced to the treatment site through an access sheath (not shown), stent, or other access or dilatation device known in the art. In addition, the device 2 may be used in conjunction with an endoscope (not shown) or other type of intracorporeal scope known in the art. The endoscope may advance through the body over a guidewire to the treatment site. Alternatively, the endoscope may be independently fed to the treatment site without the use of a guidewire. Once the treatment site has been reached, the device 2 may be fed through an access port of the endoscope to gain access to the stone 34.

While being advanced to the treatment site, the basket 4 of the device 2 may be at least partially, and preferably fully, enclosed within the sheath 10. This configuration (shown in FIG. 2) may minimize the size of the device 2 and may assist in advancing the device 2 through the endoscope. Upon exiting the endoscope and accessing the stone 34, the user may extend at least a portion of the basket 4 from the distal end 8 of the sheath 10. The basket 4 may then be manipulated relative to the stone 34 so as to capture the stone 34 within the basket 4 (as shown in FIG. 1). Once captured, the stone 34 may be retrieved by removing the device 2 from the body of the patient.

If, however, the targeted stone 34 is larger than approximately 3 mm, the stone 34 may be too large to be safely removed from the body. In these situations, the user may use the device 2 to capture and assist in immobilizing the stone 34. The user may then perform a stone-reduction process, such as, for example, laser lithotripsy, to break up or otherwise reduce the size of the stone 34. The device 4 may act as a backstop during such a process and may assist in preventing particles of the stone 34 from migrating or escaping from the treatment site during or after the stone-reduction process. In such a process, a laser fiber (not shown) or other conventional device may be used to break up the stone 34. The laser fiber 36 may be fed through an access port of an endoscope and may be activated and controlled by the user to reduce the size of the stone 34 or to fragment it into smaller pieces. Once the stone 34 has been reduced, the device 2 may act as a sweeping device to sweep stones and stone particles obtained from the reduction process out of the body.

Other embodiments of the invention will be apparent to those skilled in the art from consideration of the specification and practice of the invention disclosed herein. For example, the elongate member 6 and/or the sheath 10 may include a plurality of flexibility features configured to increase the flexibility of the device 2. The flexibility features may be formed by removing a portion of the elongate member 6 and/or the sheath 10. It is intended that the specification and examples be considered as exemplary only, with the true scope and spirit of the invention being indicated by the following claims.

What is claimed is:

1. A medical device, comprising:
    a sheath defining a lumen; and
    an elongate member movably disposed within the lumen, the elongate member including a basket having a plurality of legs, at least one leg of the plurality of legs being disposed between adjacent first and second slots defined by the elongate member, the first slot defining a first distal relief feature at a distal end of the first slot and a first proximal relief feature at a proximal end of the first slot, and the second slot defining a second distal relief feature at a distal end of the second slot and a second proximal relief feature at a proximal end of the second slot, wherein the first distal relief feature is substantially completely proximal the second distal relief feature, and the first proximal relief feature is substantially completely distal the second proximal feature.

2. The medical device of claim 1, wherein the elongate member and the basket are formed from a single piece of a material.

3. The medical device of claim 1, wherein the first and second slots extend substantially longitudinally along the elongate member.

4. The medical device of claim 1, wherein the first and second slots are formed by removing portions of the elongate member.

5. The medical device of claim 1, wherein at least one of the relief features is an extension of a corresponding slot.

6. The medical device of claim 1, wherein at least one of the relief features is a widened end of a corresponding slot.

7. The medical device of claim 1, wherein at least one of the relief features is an opening in a wall of the elongate member.

8. The medical device of claim 7, wherein the at least one relief feature has a width greater than a width of a corresponding slot.

9. The medical device of claim 1, wherein the first proximal relief feature has a first width dimension, the first distal relief feature has a second width dimension, and the first slot has a third width dimension, the first and second width dimensions being larger than the third width dimension.

10. The medical device of claim 1, further including a third slot defined by the elongate member and disposed adjacent to at least one of the first slot and the second slot, a third distal relief feature at a distal end of the third slot being longitudinally offset from an adjacent distal relief feature.

11. The medical device of claim 10, wherein the third distal relief feature is substantially completely proximal the second distal relief feature, and a third proximal relief feature at a proximal end of the third slot is substantially completely proximal the second proximal relief feature.

12. The medical device of claim 1, wherein the basket comprises at least four legs.

13. The medical device of claim 1, wherein the basket comprises a predetermined shape in an expanded position.

14. The medical device of claim 1, wherein the elongate member is substantially hollow.

15. The medical device of claim 1, wherein the first distal relief feature is completely proximal the second distal relief feature.

16. A medical retrieval device basket, comprising:
    a plurality of legs, each of the legs being defined by at least two slots of an elongate member, a first distal relief feature being disposed at a distal end of a first slot, a first proximal relief feature being disposed at a proximal end of the first slot, a second distal relief feature being disposed at a distal end of a second slot, and a second proximal relief feature being disposed at a proximal end of the second slot, wherein the first slot is adjacent the second slot, the first distal relief feature is substantially completely proximal the second distal relief feature, and the first proximal relief feature is substantially completely distal the second proximal relief feature.

17. The medical device of claim 16, wherein the at least two slots extend substantially longitudinally along the elongate member.

18. The medical device of claim 16, wherein the at least two slots are formed by removing portions of the elongate member.

19. The medical device of claim 16, wherein at least one of the relief features is an extension of a corresponding slot.

20. The medical device of claim 16, wherein at least one of the relief features is a widened end of a corresponding slot.

21. The medical device of claim 16, wherein at least one of the relief features is an opening in a wall of the elongate member.

22. The medical device of claim 21, wherein the at least one relief feature has a width greater than a width of a corresponding slot.

23. The medical device of claim 16, wherein the first proximal relief feature has a first width dimension, the first distal relief feature has a second width dimension, and the first slot has a third width dimension, the first and second width dimensions being larger than the third width dimension.

24. The medical device of claim 16, further including a third slot defined by the elongate member and disposed adjacent to at least one of the first slot and the second slot, a third distal relief feature at a distal end of the third slot being longitudinally offset from an adjacent distal relief feature.

25. The medical device of claim 24, wherein the third distal relief feature is substantially completely proximal the second distal relief feature, and a third proximal relief feature at a proximal end of the third slot is substantially completely proximal the second proximal relief feature.

26. The medical device of claim 16, wherein the basket comprises at least four legs.

27. The medical device of claim 16, wherein the basket comprises a predetermined shape in an expanded position.

28. The medical device of claim 16, wherein the elongate member is substantially hollow.

29. The medical device of claim 16, wherein the first distal relief feature is completely proximal the second distal relief feature.

30. A method of removing matter from the body of a patient, comprising:
    providing a medical device including a sheath defining a lumen, and an elongate member movably disposed within the lumen, the elongate member including a basket having a plurality of legs, at least one leg of the plurality of legs being disposed between adjacent first and second slots defined by the elongate member, the first slot defining a first distal relief feature at a distal end of the first slot and a first proximal relief feature at a proximal end of the first slot, and the second slot defining a second distal relief feature at a distal end of the second slot and a second proximal relief feature at a proximal end of the second slot, wherein the first distal relief feature is substantially completely proximal the second distal relief feature, and the first proximal relief feature is substantially completely distal the second proximal relief feature;
    advancing the medical device to a treatment site within the body of the patient;
    capturing the matter within the basket of the device; and
    removing the medical device from the body of the patient.

31. The method of claim 30, further including immobilizing the matter with the plurality of legs of the basket.

32. The method of claim 30, further including reducing the size of the matter.

33. The method of claim 30, further including sweeping at least a portion of the matter from the treatment site with the plurality of legs of the basket.

34. The method of claim 30, wherein the matter is one of a kidney stone, a struvite, a uric acid stone, a cystine stone, and a solid deposit.

35. The method of claim 30, wherein the first proximal relief feature has a first width dimension, the first distal relief feature has a second width dimension, and the first slot has a third width dimension, the first and second width dimensions being larger than the third width dimension.

36. The method of claim 30, further including a third slot defined by the elongate member and disposed adjacent to at least one of the first slot and the second slot, a third distal relief feature at a distal end of the third slot being longitudinally offset from an adjacent distal relief feature.

37. The method of claim 36, wherein the third distal relief feature is substantially completely proximal the second distal relief feature and a third proximal relief feature at a proximal end of the third slot is substantially completely proximal the second proximal relief feature.

38. The method of claim 30, wherein the first distal relief feature is completely proximal the second distal relief feature.

* * * * *